United States Patent
Chouinard et al.

(10) Patent No.: US 7,634,374 B2
(45) Date of Patent: Dec. 15, 2009

(54) METHOD FOR PERMANENT CALIBRATION BASED ON ACTUAL MEASUREMENT

(75) Inventors: Benoît Chouinard, Montréal (CA); Louis Brillon, Varennes (CA); Benoît Pelletier, Laval (CA); Sébastien Jutras, Laval (CA)

(73) Assignee: Orthosoft Inc., Montreal, Quebec (CA)

( * ) Notice: Subject to any disclaimer, the term of this patent is extended or adjusted under 35 U.S.C. 154(b) by 219 days.

(21) Appl. No.: 10/593,563

(22) PCT Filed: Apr. 26, 2005

(86) PCT No.: PCT/CA2005/000635

§ 371 (c)(1),
(2), (4) Date: Jun. 26, 2007

(87) PCT Pub. No.: WO2005/102202

PCT Pub. Date: Nov. 3, 2005

(65) Prior Publication Data

US 2007/0265715 A1    Nov. 15, 2007

Related U.S. Application Data

(60) Provisional application No. 60/564,963, filed on Apr. 26, 2004.

(51) Int. Cl.
*G06F 19/00* (2006.01)

(52) U.S. Cl. .............................. 702/85; 33/501; 73/1.01; 235/375; 356/601; 382/141; 382/152; 702/155

(58) Field of Classification Search ............... 33/501, 33/502, 503, 504, 533, 534, 535, 545, 546, 33/547, 548, 551, 559; 73/1.01, 1.79, 1.81, 73/865.8, 865.9; 235/375; 356/600, 601, 356/602, 603, 604, 605, 606, 607, 608, 609, 356/610, 611, 612, 613, 625, 626, 627, 628, 356/629, 630, 631, 632, 633, 634, 635, 636, 356/637, 638, 639, 640, 388, 394; 382/100, 382/141, 152; 702/1, 33, 34, 35, 81, 82, 702/84, 85, 97, 105, 127, 155, 156, 157, 702/158, 166, 167, 168, 170, 187, 188, 189
See application file for complete search history.

(56) References Cited

U.S. PATENT DOCUMENTS 4,303,984 A * 12/1981 Houvig ..................... 702/104

(Continued)

FOREIGN PATENT DOCUMENTS

JP           62-130160 A   *  6/1987

*Primary Examiner*—Edward R Cosimano
(74) *Attorney, Agent, or Firm*—Ogilvy Renault LLP

(57) ABSTRACT

There is described a method of manufacturing a device to be used with a computer-aided surgery system, a method of calibrating the device, and the device itself. After fabrication, the device is measured to obtain true parameters thereof. The true parameters are stored on a storage medium associated with the device and include measurement data of high precision relating to dimensions of the device as well as to relative positioning of a tracker on the device with respect to the device. The true parameters are entered into the system and when the tracker is located in the 3D environment, the device can then be located in the 3D environment with a high degree of precision using the true parameters.

28 Claims, 3 Drawing Sheets

U.S. PATENT DOCUMENTS

| | | | | |
|---|---|---|---|---|
| 4,382,215 A | * | 5/1983 | Barlow et al. | 318/568.1 |
| 4,418,392 A | * | 11/1983 | Hata | 702/91 |
| 4,672,306 A | | 6/1987 | Thong | |
| 4,845,649 A | * | 7/1989 | Eckardt et al. | 702/104 |
| 4,868,476 A | * | 9/1989 | Respaut | 318/632 |
| 5,089,979 A | * | 2/1992 | McEachern et al. | 702/91 |
| 5,347,476 A | * | 9/1994 | McBean, Sr. | 702/91 |
| 5,357,953 A | | 10/1994 | Merrick et al. | |
| 5,365,462 A | * | 11/1994 | McBean, Sr. | 702/91 |
| 5,375,073 A | * | 12/1994 | McBean | 702/91 |
| 5,377,128 A | * | 12/1994 | McBean | 702/91 |
| 5,617,857 A | | 4/1997 | Chader et al. | |
| 5,790,432 A | * | 8/1998 | Morys | 702/91 |
| 5,839,094 A | * | 11/1998 | French | 702/91 |
| 5,946,641 A | * | 8/1999 | Morys | 702/91 |
| 5,987,960 A | | 11/1999 | Messner et al. | |
| 6,347,460 B1 | | 2/2002 | Forrer et al. | |
| 6,427,129 B1 | * | 7/2002 | Lalla | 702/88 |
| 6,640,607 B2 | | 11/2003 | Abbe | |
| 2007/0108285 A1 | * | 5/2007 | Lapstun et al. | 235/454 |
| 2007/0187240 A1 | * | 8/2007 | Araya et al. | 204/424 |

* cited by examiner

METHOD FOR PERMANENT CALIBRATION BASED ON ACTUAL MEASUREMENT

CROSS-REFERENCE TO RELATED APPLICATION

The present patent application claims priority on U.S. Provisional Patent Application No. 60/564,963, filed on Apr. 26, 2004, now expired.

FIELD OF THE INVENTION

The present invention generally relates to instrumentation and, more particularly, to a method for calibrating instrumentation used in a computer-assisted surgery environment.

BACKGROUND OF THE INVENTION

Instruments and implants such as surgical instruments and orthopedic implants are manufactured according to specifications usually illustrated in manufacturing drawings. The manufacturing drawings specify dimensions and precision requirements for the manufactured instruments. These precision requirements are stricter when the instruments or implants are used in an environment such as is encountered in a Computer Assisted Surgery (CAS) system.

After the manufacturing of an instrument, comparative measurements of the manufactured instrument are made with the initial specifications. If the end result of the measurements is outside the specifications of the manufacturing drawings, the instrument is rejected. To achieve high precision, the manufacturing process can be expensive.

A CAS system creates a precision environment where a surgeon uses a computer system to track, in a 3-dimensional reference spatial system, one or more instruments and implants. The precision required varies from 0.1 mm to 1 mm in position and can also be very high in angle. The instruments and implants tracked by the CAS system have generic characteristics that need to be known by the CAS system. In addition, the CAS system needs to track the relative position of the implant or the instrument to the tracker coordinate system. This is typically done using one of various calibration techniques.

A first known calibration method consists in identifying the tip and the axis of a tool with the help of a calibration block. The block has a base plate with a pin hole located at its center to position the tip of the instrument. Around the pin hole, eight posts are placed in a quasi-circular position. The tool is equipped with a means for registering and tracking the tool in a 3D environment. For registering the tip of the instrument, the tip is positioned against the pinhole located at the center of the base plate. The system registers both the calibration block and the instrument and calculates the position of the tip of the instrument from its position in the pinhole of the calibration block. To determine the axis, the instrument is successively positioned against the eight posts located on the calibration block and registered. A second calibration method consists in using a simplified calibration block capable of positioning the tool against a reference pinhole and clamp in a known position. The system registers both the calibration block and the instrument. From the registration of the tool, the system can extrapolate the position of the tip and, since the calibration block has clamped the instrument in a known position, the system can extract the axis of the tool from the registration of the tool and the calibration block and the known position of the clamped instrument.

There is a need for a method to calibrate a tool or implant that would reduce the time spent in the operating room performing the calibration, and simplify the procedure.

SUMMARY OF THE INVENTION

Accordingly, an object of the present invention is to provide a method for permanent calibration based on actual measurement.

There is provided herein a method of manufacturing a device to be used with a computer-aided surgery system, a method of calibrating the device, and the device itself. After fabrication, the device is measured to obtain true parameters thereof. The true parameters are stored on a storage medium associated with the device and include measurement data of high precision relating to dimensions of the device as well as to relative positioning of a tracker on the device with respect to the device. The true parameters are entered into the system and when the tracker is located in the 3D environment, the device can then be located in the 3D environment with a high degree of precision using the true parameters.

It should be understood that the term "true parameters" can either be a set of points, a single point, a set of ranges within which the points can be found, or a single range within which a point can be found. The precision used to determine the points or ranges will vary depending on the instruments used to take the measurements. The instrument can be, for example, a coordinate measuring machine, an interferometer, or any other type of measuring device known in the art.

In accordance with a first broad aspect of the present invention, there is provided a method for manufacturing a device to be used with a computer aided surgery system, the method comprising: fabricating the device in accordance with its specifications, wherein the fabricating includes providing the device with a tracker of a known configuration recognizable by the computer aided surgery system; after the fabricating, measuring the device to obtain true parameters thereof, the measuring including determining a relative position of the tracker with respect to the device; and storing the true parameters in a storage medium associated with the device such that the true parameters accompany the device.

In accordance with a second broad aspect of the present invention, there is provided a method of calibrating a device to be used with a computer aided surgery system, the device having a tracker of a known configuration recognizable by the system provided thereon, the method comprising: measuring the device after fabrication to obtain true parameters thereof, the measuring including determining a relative position of the tracker with respect to the device; storing the true parameters in a storage medium associated with the device such that the true parameters accompany the device; entering the true parameters into the computer aided surgery system, including the relative position of the tracker with respect to the device; and identifying the device in a three dimensional environment of the system by using the true parameters and recognizing a position of the tracker within the system.

In accordance with a third broad aspect of the present invention, there is provided a device to be used with a computer aided surgery system, the device comprising: a tracker mounted to the device, the tracker being of a known configuration and recognizable by the system; and a storage medium associated with the device, the storage medium comprising true parameters of the device obtained by measuring the device after fabrication, the true parameters including a relative position of the tracker with respect to the device.

It should be understood that the term "storage medium" is used herein to refer to any material that holds data in any form, such as paper, transparencies, multipart forms, hard, floppy and optical disks, magnetic tape, wire, cable and fiber. For example, the true parameters can be stored on a code engraved on the device, a code printed on a sticker applied to the device, a serial number marked on the device, or any type of temporary memory such as a CD-ROM, a flash card, a USB stick, or a tape that is packaged with the device. The data can be stored electronically or not.

The code marked on the device can be in machine readable format or human readable format. It can be entered manually into a computer system, or be entered electronically by either scanning the code into the system or sending the information by other means. The code can include various types of data about the device, such as the precise measurements taken after fabrication, the relative measurements between the tip of the tool and the tracker, the configuration of the tracker, a serial number to identify the tool, etc.

At any time, the calibration data marked on the device may be validated or confirmed using known calibration methods. If the data obtained during the validation differs from the true parameters marked on the device, the user may decide which set of data the system is to use. For example, the true parameters marked on the device may be updated using the validation data. Alternatively, the system may be told to override the validation data with the true parameters.

BRIEF DESCRIPTION OF DRAWINGS

These and other features, aspects and advantages of the present invention will become better understood with regard to the following description and accompanying drawings wherein.

DESCRIPTION OF THE PREFERRED EMBODIMENT

In a preferred embodiment of the present invention, at the end of the manufacturing process, the characteristics of the instrument needed by a CAS system are precisely measured. Those measurements, unique to that instrument, are recorded on a media and constitute the permanent calibration of that instrument. At the first use in an operating room, the instrument is selected and those measured characteristics, which are its true parameters, are fed to a CAS system, which can store the information. At further use, the operator can select the instrument per its identification and the system can use the stored information or read again the information related to the true parameters of the instrument.

Figure 1:
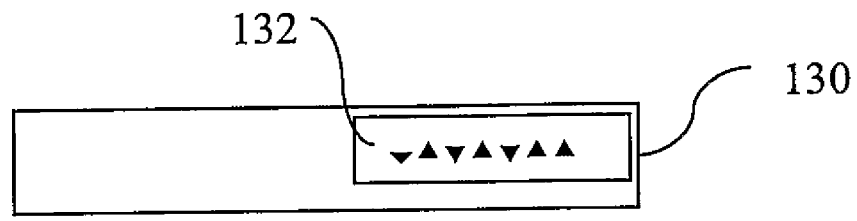
FIG. 1 is a view of an instrument with exemplary machine readable format marking.

Referring to the drawings and, more particularly, to FIG. 1, an instrument 130 with exemplary marking 132 is shown. The instrument 130 is manufactured according to manufacturing drawings containing measurement specifications and precision requirements. Once the instrument 130 is manufactured, precise measurements of the instrument are taken using for instance a Coordinate Measuring Machine (CMM), which permits a precision as high as 0.001 mm. The measurements represent the true parameters of the instrument 130 to be used in an environment requiring a high degree of precision. The marking 132 on the instrument 130, is made on a section visible to the operator.

Alternatively, typographical characters readable (not shown) by a video system and identifiable by a computer system can be used. The characters can also be entered manually by the user. However, this is more time-consuming.

The content of marking 132 can consist of an identification of the instrument including a product code, a serial number for tracking inventory or measurements made to a specified degree of precision (including ranges of measurements).

Figure 2:
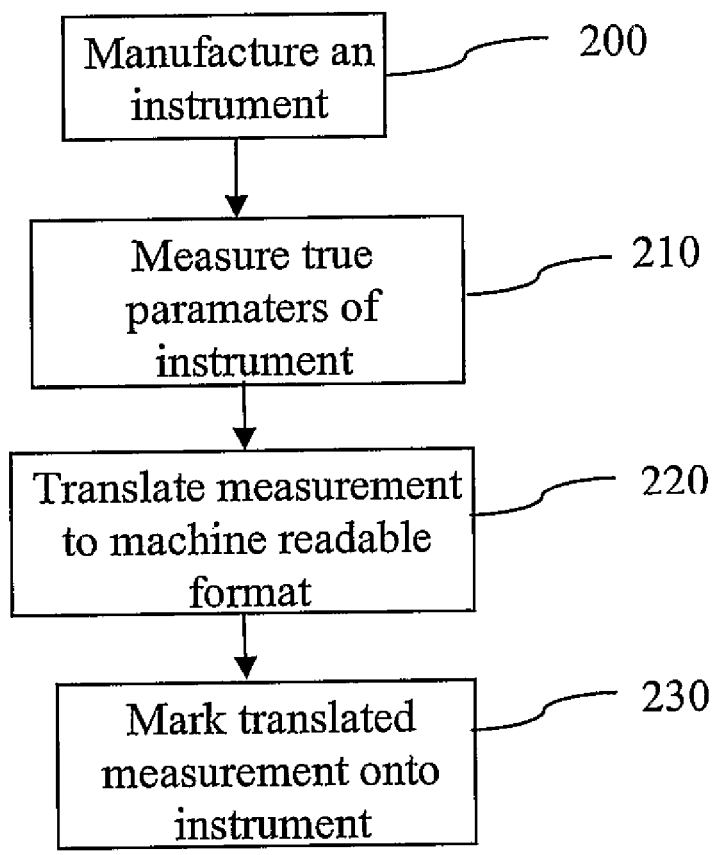
FIG. 2 is a flow chart of the method of manufacture of the device in accordance with the preferred embodiment of the present invention.

FIG. 2 relates to the method used to manufacture the device, as per the preferred embodiment of the present invention. In step 200, an instrument is manufactured according to the specifications in the manufacturing drawings. The drawings specify dimensions for the instrument with various tolerance levels. At step 210, the true parameters (dimension, plane) of the manufactured instrument required by the system are precisely measured. These measurements are converted to machine readable format at step 220. Then, at step 230, the converted measurements are marked onto the instrument.

The process illustrated in FIG. 2 reduces the cost of manufacturing by preventing instruments that do not fall within the tolerance requirements from being rejected. These instruments are usually rejected because their true parameters differ too greatly from the specifications and therefore, they would lead to precision errors in an environment such as a CAS. However, by providing the true parameters on the instrument, the CAS system can simply read the true parameters from the marking on the device itself and eliminate the possibility of error due to imprecise measurements. The method of FIG. 2 also permits the use of the instrument in a high precision environment. The measurements obtained using high-precision measurement devices immediately after fabrication can provide measurements of higher precision than the standard calibration techniques used in the operating room. Therefore, the data used by the CAS is more precise.

The described method eliminates the calibration previously required in the operating room. However, to properly ensure the tool is registered, a validation step can be used (not shown on the figure). When a tool is used by the CAS system, to validate the information marked on the tool in relation to the actual tool, the system validates the position of the tracker in relation to an extremity of the tool. This is particularly useful in the case where the tracker may have moved or the tip of the instrument is bent after having been dropped.

Figure 3:
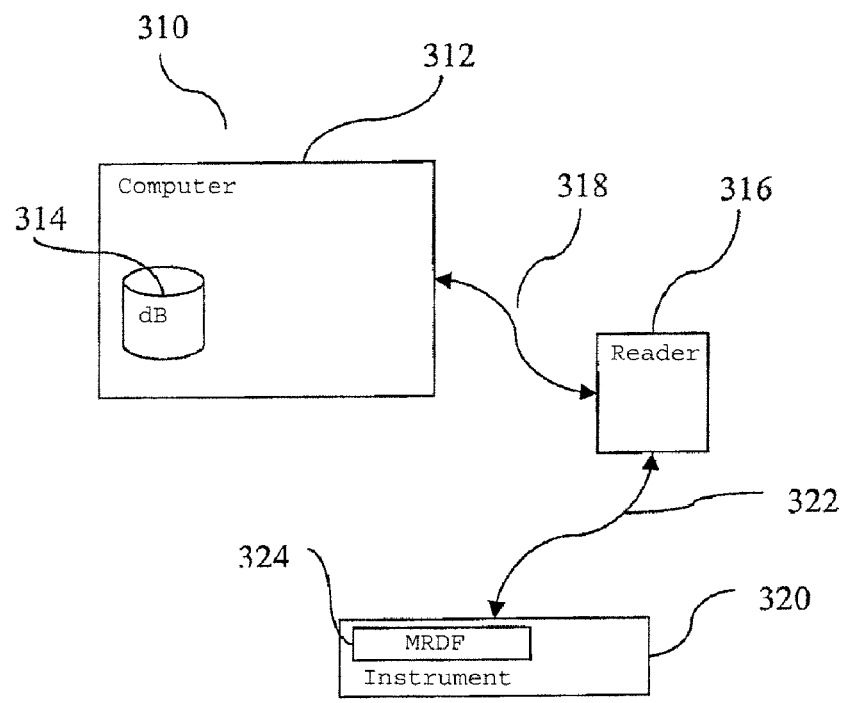
FIG. 3 is a view of the system, in accordance with a preferred embodiment of the present invention.

FIG. 3 shows a system using the instrument illustrated in FIG. 1. The system used for identifying an instrument in a high precision environment is generally shown at 310. A computer 312, comprising a database (dB) 314 is shown. The database 314 may already contain part of the geometrical characteristics of the instruments (such as generic information). The information can be completed with the results of the measurements taken in step 210 in order to take into account the small variations from one instrument to another. The computer 312 can be part of a CAS system (not shown). The computer 312 is connected, through link 318, to a reader 316.

The reader 316 can be mechanical, optical, electromagnetic, RF or other type generally known in the art of readers capable of reading machine code format. The data may be sent to the reader in an active or in a passive way.

Figure 4:
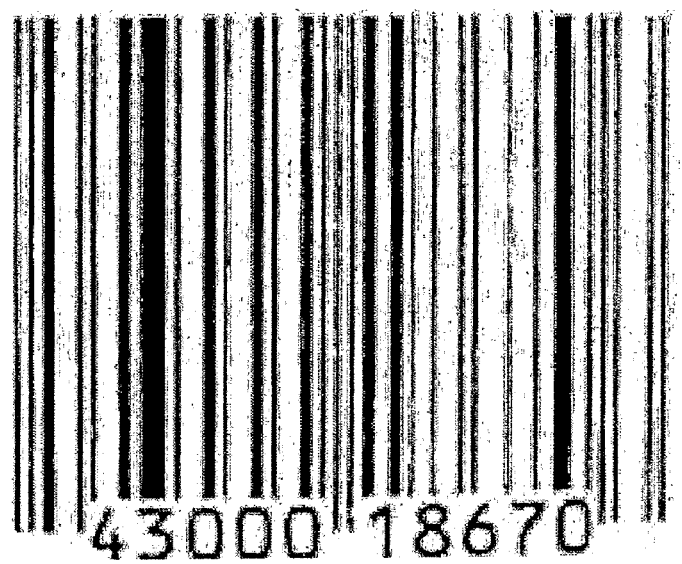
FIG. 4 is an example of a linear bar code.
Figure 5A:
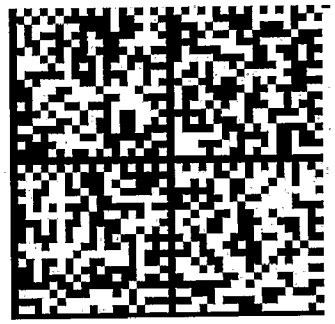
FIGS. 5a and 5b are examples of 2-dimensional matrix bar codes.
Figure 5B:
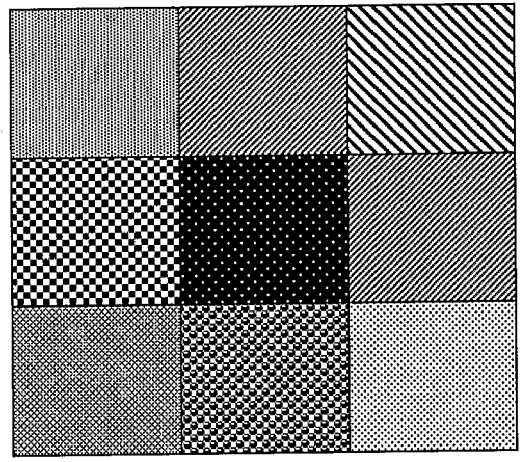

The machine readable format may be a bar code. The bar code format can be a linear format as shown in FIG. 4 or a 2-dimensional matrix bar code permitting higher data density marking as shown in FIGS. 5a and 5b.

The instrument 320 is marked with machine reader format data (MRDF) 324. The data 324 marked on the instrument 320 contains the true parameters of the instrument 320. These true parameters relate to identification of the instrument and accurate dimensions of the instrument 320 measured after manufacturing.

When the data 324 on the instrument 320 is read by the reader 316 and transmitted to computer 312, through link 322, computer 312 identifies the instrument 320. It can get generic characteristics about the instrument 320 from the database 314. With the precise measurements read from the machine reader format data 324, the computer 312 can adjust the characteristics of instrument 320.

Another method for entering the data to be marked on the instrument is through manual data entry. The data related to the serial number of the instrument and the measured characteristics are keyed into a device capable of converting to a machine readable format. That converted data is then marked onto the instrument.

As another method, the instrument 320 can be packaged with a CD-ROM or another temporary storage medium containing the characteristics of the instrument. It is to be understood that database 314 can be a temporary storage media and not necessarily a permanent database.

As another alternative, the database 314 can be remotely accessed through a communication means.

Figure 6:
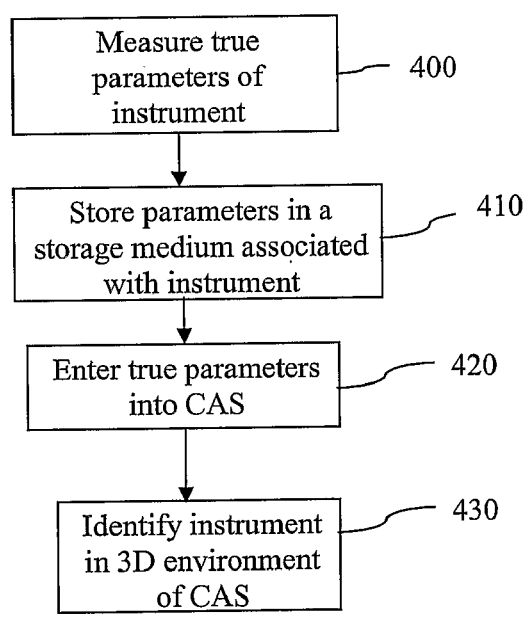
FIG. 6 is a flow chart of the method of calibration of the device in accordance with the preferred embodiment of the present invention.

FIG. 6 relates to the method used to calibrate the device, as per the preferred embodiment of the present invention. The instrument, which has been fabricated with a tracker having a known configuration and recognizable by a CAS, is measured to determine its true parameters 400. The true parameters are stored on a storage medium (electronically or not) associated with the instrument 410. The true parameters are entered into the CAS system (manually or automatically) 420. The CAS system then uses the true parameters to locate the instrument in the 3D environment 430. Since the true parameters have the dimensions of the tool and the relative positioning of the tip of the tool with respect to the tracker, and the tracker is of a known configuration, when the system identifies the tracker and is able to position it in the 3D environment, it can then position the tip of the tool and all dimensions which are relative to the tip of the tool, allowing it to provide an image of the tool on a display in the 3D environment.

The tracker used with the present invention may be of any known type in the art, such as optical, magnetic, RF, passive, active, etc.

While illustrated in the block diagrams as groups of discrete components communicating with each other via distinct data signal connections, it will be understood by those skilled in the art that the preferred embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present preferred embodiment.

The embodiments of the invention described above are intended to be exemplary only. The scope of the invention is therefore intended to be limited solely by the scope of the appended claims.

We claim:

1. A method for manufacturing a device to be used with a computer aided surgery system, the method comprising:

fabricating said device in accordance with its specifications, wherein said fabricating comprises providing said device with a tracker of a known configuration recognizable by said computer aided surgery system;

after said fabricating, measuring said device to obtain true parameters thereof, said measuring comprising determining a relative position of said tracker with respect to said device; and storing said true parameters in a storage medium associated with said device such that said true parameters accompany said device.

2. A method as claimed in claim 1, wherein said storing said true parameters comprises storing said true parameters on a disc that is packaged with said device.

3. A method as claimed in claim 1, wherein said providing said device with a tracker comprises providing a passive optical tracker.

4. A method as claimed in claim 1, wherein said measuring said device comprises measuring using an apparatus that allows precision of 0.001 mm.

5. A method as claimed in claim 4, wherein said apparatus is a coordinate measuring machine.

6. A method as claimed in claim 1, wherein said storing said true parameters comprises marking said device with said true parameters by placing a visible code on said device, said code representing said true parameters.

7. A method as claimed in claim 6, wherein said marking said device comprises marking said device with said true parameters in a machine readable format.

8. A method as claimed in claim 7, wherein said marking said device with said true parameters in a machine readable format comprises using a linear bar-code format.

9. A method of calibrating a device to be used with a computer aided surgery system, said device having a tracker of a known configuration recognizable by said system provided thereon, the method comprising:

measuring said device after fabrication to obtain true parameters thereof, said measuring including determining a relative position of said tracker with respect to said device;

storing said true parameters in a storage medium associated with said device such that said true parameters accompany said device;

entering said true parameters into said computer aided surgery system, including said relative position of said tracker with respect to said device; and identifying said device in a three dimensional environment of said system by using said true parameters and recognizing a position of said tracker within said system.

10. A method as claimed in claim 9, wherein said storing said true parameters comprises storing said true parameters on a disc that is packaged with said device.

11. A method as claimed in claim 9, wherein said providing said device with a tracker comprises providing a passive optical tracker.

12. A method as claimed in claim 9, wherein said identifying said device comprises associating said true parameters with generic parameters stored in said system for said device, and updating said generic parameters to correspond to said true parameters.

13. A method as claimed in claim 9, wherein said measuring said device comprises measuring using an apparatus that allows precision of 0.001 mm.

14. A method as claimed in claim 13, wherein said apparatus is a coordinate measuring machine.

15. A method as claimed in claim 9, further comprising confirming said true parameters entered into said system by placing said device into a standard calibration block.

16. A method as claimed in claim 15, wherein said identifying said device comprises updating said system with corrected true parameters if data from said standard calibration block differs from said true parameters.

17. A method as claimed in claim 9, wherein said storing said true parameters comprises marking said device with said true parameters by placing a visible code on said device, said code representing said true parameters.

18. A method as claimed in claim 17, wherein said marking said device comprises marking said device with said true parameters in a machine readable format.

19. A method as claimed in claim 18, wherein said marking said device with said true parameters in a machine readable format comprises using a linear bar-code format.

20. A method as claimed in claim 18, wherein said entering said code into said system comprises scanning a bar-code into said system.

21. A device to be used with a computer aided surgery system, the device comprising:
 a tracker mounted to said device, said tracker being of a known configuration and recognizable by said system; and
 a storage medium associated with said device, said storage medium comprising true parameters of said device obtained by measuring said device after fabrication, said true parameters including a relative position of said tracker with respect to said device.

22. A device as claimed in claim 21, wherein said storage medium is a disc that is packaged with said device.

23. A device as claimed in claim 21, wherein said tracker is a passive optical tracker.

24. A device as claimed in claim 21, wherein said tracker is integrally formed with said device.

25. A device as claimed in claim 21, wherein said true parameters are measured with an apparatus providing a precision of 0.001 mm.

26. A device as claimed in claim 21, wherein said storage medium is a code inscribed on said device, said code comprising said true parameters.

27. A device as claimed in claim 26, wherein said code is in a machine-readable format.

28. A device as claimed in claim 27, wherein said machine-readable format is a linear bar-code format.

* * * * *